US00PP36747P2

(12) United States Plant Patent
Mathey

(10) Patent No.: US PP36,747 P2
(45) Date of Patent: Jun. 17, 2025

(54) ***BIGNONIA* PLANT NAMED 'SMNBFW'**

(50) Latin Name: *Bignonia capreolata*
Varietal Denomination: SMNBFW

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/947,467

(22) Filed: Nov. 14, 2024

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Bignonia* plant named 'SMNBFW', characterized by its upwardly vining plant habit; vigorous growth habit; freely branching habit; dense and bushy appearance; dark green-colored leaves; freely flowering habit; dark red-colored salverform flowers with bright yellow-colored throats; and good garden performance.

2 Drawing Sheets

Figure 1:
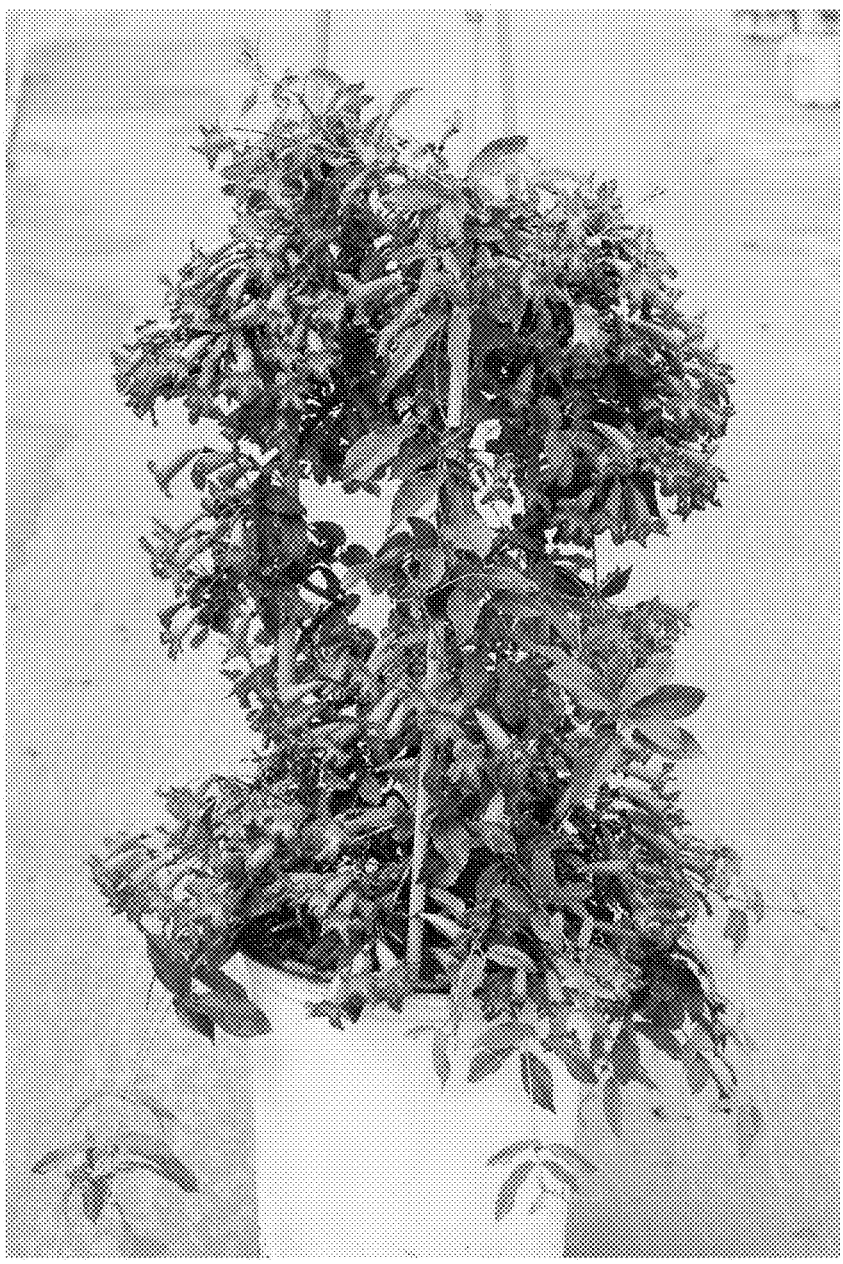

Botanical designation: *Bignonia capreolata*.
Cultivar denomination: 'SMNBFW'.

BACKGROUND OF THE INVENTION

The present invention relates to a new and distinct cultivar of *Bignonia* plant, botanically known as *Bignonia capreolata*, commonly referred to as Crossvine or Trumpet Flower and hereinafter referred to by the name 'SMNBFW'.

The new *Bignonia* is a product of a planned breeding program conducted by the Inventor in Grand Haven, Michigan. The objective of the breeding program was to develop new freely flowering *Bignonia* plants with healthy and attractive leaf coloration.

The new *Bignonia* plant originated from a cross-pollination during the summer of 2014 of *Bignonia capreolata* 'Dragon Lady', not patented, as the female, or seed, parent with *Bignonia capreolata* 'Tangerine Beauty', not patented, as the male, or pollen, parent. The new *Bignonia* plant was discovered and selected by the Inventor during the summer of 2019 as a single flowering plant within the progeny of the stated cross-pollination in a controlled environment in Grand Haven, Michigan.

Asexual reproduction of the new *Bignonia* plant by softwood cuttings in a controlled greenhouse environment in Grand Haven, Michigan since the summer of 2019 has shown that the unique features of this new *Bignonia* plant are stable and reproduced true to type in successive generations of asexual reproduction.

SUMMARY OF THE INVENTION

Plants of the new *Bignonia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNBFW'. These characteristics in combination distinguish 'SMNBFW' as a new and distinct *Bignonia* plant:

1. Upwardly vining plant habit.
2. Vigorous growth habit.
3. Freely branching habit; dense and bushy appearance.
4. Dark green-colored leaves.
5. Freely flowering habit.
6. Dark red-colored salverform flowers with bright yellow-colored throats.
7. Good garden performance.

Plants of the new *Bignonia* can be compared to plants of the female parent, 'Dragon Lady'. In side-by-side comparisons, plants of the new *Bignonia* differ primarily from plants of 'Dragon Lady' in flower color as plants of the new *Bignonia* have dark red-colored flowers with bright yellow-colored throats whereas plants of 'Dragon Lady' have red-colored flowers with darker red-colored throats.

Plants of the new *Bignonia* can be compared to plants of the male parent, 'Tangerine Beauty'. In side-by-side comparisons, plants of the new *Bignonia* differ primarily from plants of 'Tangerine Beauty' in flower size as plants of the new *Bignonia* have smaller flowers than plants of 'Tangerine Beauty'. In addition, flower petals of plants of the new *Bignonia* are not as rugose as flower petals of plants of 'Tangerine Beauty'.

Plants of the new *Bignonia* can be compared to plants of *Bignonia capreolata* 'Jekyll', not patented. In side-by-side comparisons, plants of the new *Bignonia* differ primarily from plants of 'Jekyll' in the following characteristics:

1. Leaves of plants of the new *Bignonia* are larger and darker green in color than leaves of plants of 'Jekyll'.
2. Flowers of plants of the new *Bignonia* are larger than flowers of plants of 'Jekyll'.
3. Plants of the new *Bignonia* have dark red-colored flowers with bright yellow-colored throats whereas plants of 'Jekyll' have lighter red-colored flowers with less conspicuous yellow-colored throats.

Plants of the new *Bignonia* can also be compared to plants of *Bignonia capreolata* 'Atrosanguinea', not patented. In side-by-side comparisons, plants of the new *Bignonia* differ primarily from plants of 'Atrosanguinea' in flower color as plants of the new *Bignonia* have dark red-colored flowers with bright yellow-colored throats whereas plants of 'Atrosanguinea' have red-colored flowers with darker red-colored throats.

BRIEF DESCRIPTION OF THE PHOTOGRAPHS

The accompanying colored photographs illustrate the overall appearance of the new *Bignonia* plant showing the colors as true as it is reasonably possible to obtain in colored reproductions of this type. Colors in the photographs may differ slightly from the color values cited in the detailed botanical description which accurately describe the colors of the new *Bignonia* plant.

The photograph on the first sheet (FIG. 1) is a side perspective view of a typical flowering plant of 'SMNBFW' grown in a container.

Figure 2:
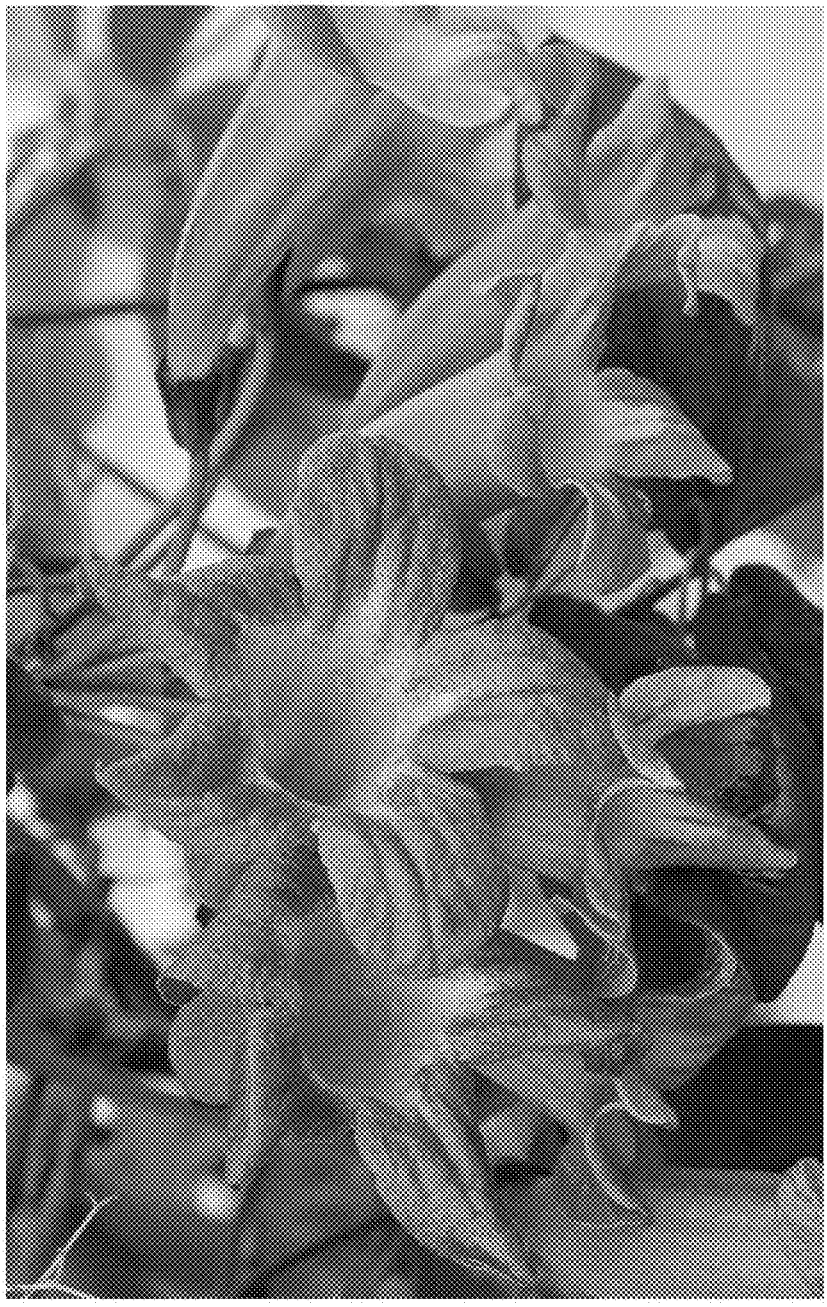

The photograph on the second sheet (FIG. 2) is a close-up view of typical flowers of 'SMNBFW'.

DETAILED BOTANICAL DESCRIPTION

The following observations, measurements and values describe plants grown during the spring in three-gallon containers with pyramidal trellises in a polyethylene-covered greenhouse in Grand Haven, Michigan and under cultural practices typical of commercial *Bignonia* production. During the production of the plants, day temperatures ranged from 18° C. to 27° C. and night temperatures ranged from 5° C. to 10° C. Plants were three years old when the photographs and the description were taken. In the description, color references are made to The Royal Horticultural Society Colour Chart, 2015 Edition, except where general terms of ordinary dictionary significance are used.

Botanical classification: *Bignonia capreolata* 'SMNBFW'.

Parentage:

- *Female, or seed, parent.*—*Bignonia capreolata* 'Dragon Lady', not patented.
- *Male, or pollen, parent.*—*Bignonia capreolata* 'Tangerine Beauty', not patented.

Propagation:

- *Type*.—By softwood cuttings.
- *Time to initiate roots, summer*.—About 60 days at temperatures ranging from 18° C. to 27° C.
- *Time to produce a rooted young plant, summer*.—About 70 days at temperatures ranging from 18° C. to 27° C.
- *Root description*.—Medium in thickness and fleshy; typically light brown in color, actual color of the roots is dependent on substrate composition, water quality, fertilizer, substrate temperature and physiological age of roots.
- *Rooting habit*.—Moderately freely branching habit; medium density.

Plant description:

- *Plant form and growth habit*.—Perennial shrub; upwardly vining plant habit; vigorous growth habit and rapid growth rate.
- *Branching habit*.—Freely branching habit, dense and bushy growth habit with about five primary lateral branches each with numerous secondary lateral branches developing per plant.
- *Plant height*.—Mature vines will attain a length of about 3.7 meters to 9.1 meters.
- *Plant diameter* (*area of spread*).—Mature vines will attain a spread of about 1.8 meters to 2.7 meters.

Lateral branch description:

- *Length*.—About 1.2 meters.
- *Diameter*.—About 5 mm.
- *Internode length*.—About 5 cm.
- *Strength*.—Strong and flexible.
- *Aspect*.—Plants can be trellised or staked from erect to horizontal.
- *Texture, developing*.—Smooth glabrous.
- *Texture, fully developed*.—Woody.
- *Color, developing*.—Close to 146A.
- *Color, when woody*.—Close to 200C to 200D.

Leaf description:

- *Arrangement*.—Opposite, compound leaves are bifoliate.
- *Leaf length*.—About 9 cm.
- *Leaf width*.—About 2 cm.
- *Leaflet length*.—About 4.5 cm.
- *Leaflet width*.—About 2 cm.
- *Leaflet shape*.—Narrowly elliptic to oblanceolate.
- *Leaflet apex*.—Acute.
- *Leaflet base*.—Obtuse.
- *Leaflet margin*.—Entire.
- *Leaflet texture, upper and lower surfaces*.—Smooth, glabrous.
- *Leaflet venation pattern*.—Pinnate.
- *Leaflet color*.—Developing leaflets, upper and lower surfaces: Close to 146B. Fully expanded leaflets, upper surface: Close to NN137B; venation, close to 146C. Fully expanded leaflets, lower surface: Close to 147B; venation, close to 146C.
- *Petioles*.—Length: About 5 mm. Diameter: About 1 mm. Texture, upper and lower surfaces: Smooth, glabrous. Color, upper and lower surfaces: Close to 146C.

Flower description:

- *Flower appearance and arrangement*.—Single salverform flowers arranged in axillary clusters; freely flowering habit with about two to three flowers per cluster and about 1,000 flowers developing per plant during the flowering season; flower face mostly outwardly to slightly downward.
- *Fragrance*.—None detected.
- *Natural flowering season*.—Plants flower in May and June in Michigan; individual flowers last about two to three weeks on the plant; flowers not persistent.
- *Flower buds*.—Length: About 4 cm. Diameter: About 1 cm. Shape: Spatulate. Color, upper surface: Close to 178B. Color, lower surface: Close to 162B.
- *Flower diameter*.—About 4 cm.
- *Flower depth*.—About 4.5 cm.
- *Flower throat diameter*.—About 1.5 cm.
- *Flower tube length*.—About 3.5 cm.
- *Flower tube diameter, proximally*.—About 5 mm.
- *Petals*.—Quantity and arrangement: Five fused petals arranged in a single whorl and fused at the base into a tube. Lobe length: About 1.5 cm. Lobe width: About 1.2 cm. Shape: Elliptic. Apex: Obtuse and occasionally emarginate. Base: Fused. Margin: Entire. Texture, upper and lower surfaces, lobes:

Smooth, glabrous; slightly coriaceous. Texture, throat: Smooth, glabrous. Texture, tube: Smooth, glabrous. Color: When opening and fully opened, upper surface: Close to 181B and towards the throat, close to 12B. When opening and fully opened, lower surface: Close to 178B. Throat: Close to 12B; proximally, close to 178B. Tube: Close to 162B.

*Sepals*.—Quantity and arrangement: Five sepals fused into a cup-shaped calyx. Calyx length: About 7 mm. Calyx diameter: About 5 mm. Texture, upper and lower surfaces: Smooth, glabrous. Color, upper and lower surfaces: Close to N186C and at the base, close to 146B.

*Peduncles*.—Length: About 2.5 cm. Diameter: About 2 mm. Strength: Strong. Aspect: About 20° to 60° from stem axis. Texture: Smooth, glabrous. Color: Close to 146B.

*Reproductive organs*.—Stamens: Quantity per flower: Four. Filament length: About 3 cm. Filament color: Close to 8B. Anther length: About 4 mm. Anther shape: Oblong. Anther color: Close to 8B. Pollen amount: Moderate. Pollen color: Close to 8D. Pistils: Quantity per flower: One. Pistil length: About 3 cm. Stigma shape: Spatulate. Stigma color: Close to 36D. Style length: About 2.75 cm. Style color: Close to 36D. Ovary color: Close to 144B. Seeds and fruits: To date, seed and fruit production have not been observed on plants of the new *Bignonia*.

Garden performance: Plants of the new *Bignonia* have been observed to have good garden performance and to tolerate rain, wind and to be suitable for USDA Zones 6 through 9.

Pathogen & pest resistance: To date, plants of the new *Bignonia* have not been shown to be resistant to pathogens and pests common to *Bignonia* plants.

It is claimed:

1. A new and distinct *Bignonia* plant named 'SMNBFW' as herein illustrated and described.

* * * * *